(12) United States Patent
Christiansen

(10) Patent No.: US 8,480,627 B2
(45) Date of Patent: Jul. 9, 2013

(54) INTRODUCER AND DEPLOYMENT HANDLE FOR SPLITTABLE SHEATH HAVING FLUSHING CHAMBER

(75) Inventor: Frank Karhu Christiansen, Haslev (DK)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/369,927

(22) Filed: Feb. 9, 2012

(65) Prior Publication Data
US 2012/0215171 A1    Aug. 23, 2012

(30) Foreign Application Priority Data

Feb. 18, 2011    (GB) .................................. 1102861.0

(51) Int. Cl.
*A61M 5/178*    (2006.01)

(52) U.S. Cl.
USPC ............. 604/167.01; 604/164.01; 604/164.05

(58) Field of Classification Search
USPC ...... 604/309, 207, 289, 523, 95.01, 524–529, 604/264, 108, 102.01, 48, 332, 334, 167.01, 604/164.01, 164.05; 623/1.11; 606/108
See application file for complete search history.

(56) References Cited

U.S. PATENT DOCUMENTS

| | | | |
|---|---|---|---|
| 5,261,887 A * | 11/1993 | Walker | 604/161 |
| 5,957,930 A | 9/1999 | Vrba | |
| 6,248,092 B1 * | 6/2001 | Miraki et al. | 604/96.01 |
| 6,544,209 B1 * | 4/2003 | Drasler et al. | 604/22 |
| 7,048,711 B2 * | 5/2006 | Rosenman et al. | 604/95.04 |
| 2007/0010867 A1 | 1/2007 | Carter et al. | |
| 2009/0018529 A1 | 1/2009 | Hoffman et al. | |
| 2009/0270969 A1 * | 10/2009 | Fargahi et al. | 623/1.11 |
| 2009/0319018 A1 | 12/2009 | Moehl et al. | |
| 2010/0100074 A1 * | 4/2010 | Smith et al. | 604/533 |
| 2012/0041537 A1 * | 2/2012 | Parker et al. | 623/1.11 |
| 2012/0059448 A1 * | 3/2012 | Parker et al. | 623/1.11 |

FOREIGN PATENT DOCUMENTS

| | | | |
|---|---|---|---|
| WO | 2007005799 A1 | 1/2007 | |
| WO | 2007013902 A2 | 2/2007 | |

\* cited by examiner

*Primary Examiner* — Nicholas Lucchesi
*Assistant Examiner* — Benjamin Koo
(74) *Attorney, Agent, or Firm* — Richard J. Godlewski

(57) ABSTRACT

An introducer assembly is provided with a handle assembly (10) which enables automatic retraction and splitting of a sheath (12) of the assembly. The handle includes a drum (22) onto which the sheath (12) can be wound, as well as a cutting blade (30) and a locking assembly (34). The locking assembly (34) provides for flushing of the space between the sheath (12) and inner catheter or other element (14), in a manner in which the handle assembly (10) is not filled with flushing fluid. The locking assembly (34) also provides for clamping of the sheath (12) during transportation and initial insertion of the introducer assembly into a patient and for release of the sheath (12) after flushing and when it is desired to retract the sheath (12). Once so released, the sheath (12) can be retracted and automatically split by means of the cutting blade (30).

18 Claims, 1 Drawing Sheet

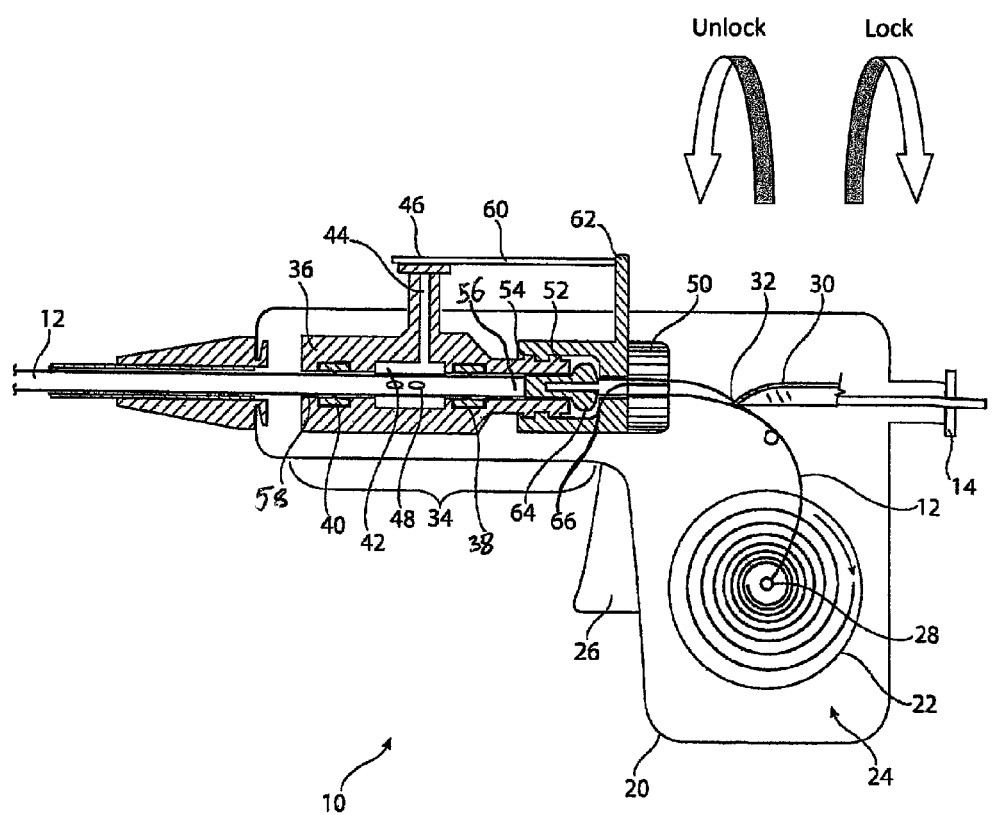

INTRODUCER AND DEPLOYMENT HANDLE FOR SPLITTABLE SHEATH HAVING FLUSHING CHAMBER

TECHNICAL FIELD

The present invention relates to a deployment handle for a splittable sheath and to a medical introducer assembly including such a deployment handle.

BACKGROUND OF THE INVENTION

The use of introducer assemblies designed to deploy implantable medical devices endoluminally is extensive in light of the many clinical and physiological advantages this provides. Such introducer devices are commonly inserted percutaneously into a patient from a location a significant distance from the site at which the device is to be implanted. For instance, aortic medical devices are often inserted through the patient's femoral artery. As a consequence, introducer assemblies have significant lengths, some well over one to one and a half meters.

Often, the introducer assembly must follow a tortuous path through the patient's vasculature, with the result that it will be curved and twisted by the time its distal end, which carries the medical device, reaches the site at which the device is to be implanted.

Moreover, in order to treat some medical conditions, the implantable medical device may itself have a substantial length. Devices having a length of 100 to 200 millimeters or more are not uncommon.

These characteristics can lead to it being necessary to impart a substantial force on the introducer assembly, particularly at the start of the deployment procedure. Moreover, in the case of a long medical device, the components of the introducer assembly need to be moved by substantial distances. For instance, the outer sheath, which covers the implantable medical device during transportation and insertion of the introducer assembly into the patient, must typically be retracted by at least the length of the medical device. This can cause difficulties at the proximal end of the introducer assembly, that is at its external handle section, in terms of the distance to be covered to retract the sheath and the consequent length of the handle section of the assembly. It is known to provide sheaths which can be split and then rolled so as to reduce the length of the handle section.

While a splittable sheath can resolve some of the disadvantages mentioned above, their structure makes it difficult to provide mechanical assistance for operating the introducer assembly, particularly due to the need to flush the assembly before use and to provide a substantially fluid sealed assembly to prevent undesired fluid loss from the patient.

DISCLOSURE OF THE INVENTION

The present invention seeks to provide an improved deployment handle for a splittable sheath and to an introducer assembly including such a deployment handle.

According to an aspect of the present invention, there is provided an introducer assembly for the deployment of an implantable medical device, the assembly including a proximal end and a distal end; a sheath; a carrier element for carrying a medical device at the distal end of the assembly, the carrier element being locatable in the sheath; a flushing unit located over the sheath at the proximal end of the assembly, the flushing unit including a flushing fluid chamber provided with first and second seals either end thereof, the seals sealing over the sheath, the sheath being provided with at least one hole therein located in the flushing fluid chamber, and a sealing element located proximally of the flushing chamber for sealing the proximal end of the sheath; wherein fluid can be flushed from the flushing fluid chamber between the sheath and the carrier element.

Typically, there will be a gap or space between the sheath and carrier element.

The assembly is particularly suitable for a splittable sheath in that it enables flushing of the sheath in an efficient manner and especially of the distal part of the sheath only, that is distally of the flushing port.

Advantageously, the assembly includes a manipulation unit at its proximal end, wherein the flushing unit forms part of the manipulation unit, the manipulation unit including a splitting element operable to split the sheath, said splitting element being located proximal of the flushing unit. The splitting element preferably includes a blade arranged to cut the sheath in a longitudinal direction.

The preferred embodiment includes a reel onto which split sheath material can be wound, there advantageously being provided a control actuator for controlling the rotation of the reel. The preferred arrangement is such that the proximal part of the assembly, reel and handle unit included, is not flushed with flushing fluid.

In a practical embodiment, the sealing element includes a compression element arranged to compress the sheath onto the carrier element, thereby to close the space between the sheath and the carrier element at the location of the compression element. The compression element preferably includes a collet clamp.

Preferably, the flushing unit includes a port for coupling to a source of flushing fluid, the driving element including a barrier element which overlies the port when the driving unit is in a configuration other than that which closes the compression element.

According to another aspect of the present invention, there is provided an introducer assembly for the deployment of an implantable medical device, the assembly including: a proximal end and a distal end; a splittable sheath; a carrier element for carrying a medical device at the distal end of the assembly, the carrier element being locatable in the sheath with a space therebetween; a flushing unit located over the sheath at the proximal end of the assembly, the flushing unit including a flushing fluid chamber provided with first and second seals either end thereof, the seals sealing over the splittable sheath, the splittable sheath being provided with at least one hole therein located in the flushing fluid chamber, and a sealing element located proximally of the flushing chamber for sealing the proximal end of the sheath, the sealing element including a collet clamp arranged to compress the sheath onto the carrier element, thereby to close the space between the sheath and the carrier element at the location of the collet clamp; a manipulation unit at the proximal end of the assembly, wherein the flushing unit forms part of the manipulation unit, the manipulation unit including means to cause splitting of the sheath, said splitting means being located proximal of the flushing unit; the manipulation unit including a reel onto which split sheath material can be wound; wherein fluid can be flushed from the flushing fluid chamber into the space between the sheath and the carrier element.

BRIEF DESCRIPTION OF THE DRAWING

Embodiments of the present invention are described below, by way of example only, with reference to the accompanying drawing, in which the sole FIGURE is a schematic view in side elevation of a distal end of an introducer assembly showing an embodiment of handle assembly with a part of its cover removed.

DESCRIPTION OF THE PREFERRED EMBODIMENTS

Referring to the FIGURE, there is shown in schematic form an embodiment of handle assembly 10 which forms part of an introducer assembly and could be described as a manipulation unit. The other components of the introducer assembly can be of conventional type, including for example an elongate sheath 12 of substantial length (in excess of one meter in many cases), within which there is provided an inner catheter, cannula or pusher rod 14 which extends from a proximal-most position typically all the way to the distal end of the sheath 12 (not shown in the FIGURE). The inner element 14 will typically include a lumen for a guide wire and will also be provided with components for holding an implantable medical device thereto, such as one or more a constraining devices. These components are known in the art and therefore not described in detail herein.

The handle assembly 10 provides in the preferred embodiment a plurality of functions, including splitting the sheath 12, rolling this onto a spool or drum within the handle assembly 10, and flushing the sheath 12 prior to use. The flushing mechanism, as described below, has a structure such that the casing of the handle assembly 10 is not filled with flushing fluid, which avoids the need to provide a fluid-tight handle assembly 10 or one which can operate when fluid filled.

The handle assembly 10 includes a casing 20, of which only one half is shown in the FIGURE but which would typically include a second half or cover to enclose the shown components of the handle assembly 10. Within the casing 20 there is provided a spool or drum 22 which is rotated by a spiral spring 24 shown in schematic form in the FIGURE. Coupled to the drum 22 is a trigger mechanism 26 which operates to control rotation of the drum 22, blocking rotation when not actuated and releasing the drum for rotation under the force of the coil spring 24 when pressed. The mechanism of the trigger 26 can be of known type, for instance having one or more teeth which engage a toothed gear wheel on the drum.

The spring 24, being in this embodiment a spiral spring, has a first end fixed in relation to the drum and a second end fixed in relation to the casing 20. The spring is normally set in a compressed or wound state such that it will unwind when released by the trigger 26, thereby to impart a rotational motion to the drum 22.

A proximal end 28 of the sheath 12 is also coupled to the drum 22, typically to a spool thereof, so as to wind onto the drum 22 when this is made to rotate. Winding of the end 28 on the drum 22 results in retraction of the sheath 12, as is explained in further detail below.

Also located within the casing 20, at a position close to the inner element 14, is a cutting blade 30, which is aligned in the longitudinal direction of the inner element 14 and of the introducer assembly. The cutting blade is positioned so as to sever the sheath 12 longitudinally at a location 32. Conveniently, the cutting blade can be held to the casing by a suitable holding element, a design and form for which being readily devisable by the skilled person.

Located distally of the cutting blade 30, there is provided a locking and flushing assembly 34. The assembly 34 includes a housing element 36 which comprises a central passage 58 through which the sheath 12 can pass, as well as the inner element 14 which resides within the sheath 12. The housing element 36 includes proximal and distal seals 38, 40, respectively, which may be in the form of annular sealing elements, most simply O-ring seals but in the embodiment shown being in a form of a flat ring having an inwardly extending annular rim which presses against the sheath 12. The proximal and distal seals 38, 40 are located either side of a flushing chamber 42 of the housing element 36.

The flushing chamber 42 is coupled to a tube or conduit 44 which leads to a luer fitting 46 which can be coupled to a syringe or other source of flushing fluid. The seals 38, 42, thus close off the flushing chamber 42 in a substantially fluid-tight manner.

As can be seen in the FIGURE, close to its proximal end, the sheath 12 provided with one or more flushing apertures 48, these being located within the flushing chamber 42 when the introducer assembly is in its assembled but pre-used configuration. The apertures 48 provide coupling to the space between the sheath 12 and inner element 14.

Located at the proximal end of the flushing chamber 42 is a locking cap 50 which is at its distal end provided with an internal screw thread 52 which co-operates with an external screw thread 54 provided at a neck portion 56 of the flushing chamber 42. The locking cap 50 can thus be rotated relative to the unit 42 such that in one direction the cap 50 also moves towards the flushing chamber 42, in a locking configuration, whereas in the other direction it moves away from the flushing chamber 42, towards an unlocking configuration.

Attached to the locking cap 50 is a flushing shield 60 which in one embodiment may be in the form of a barrier element or panel which moves with the locking cap 50, from a position in which it overlies the luer fitting 46 to a position in which it is free from the fitting 46, thereby to enable coupling of a flushing syringe or other source of flushing fluid to the luer fitting 46. As can be seen in the FIGURE, in this embodiment, the flushing shield 60 is coupled to the locking cap 50 by means of a radially extending arm 62.

Located within the locking cap 50 and also within the end 56 of the unit 42 is a collet clamp 64. The collet clamp 64 is located concentrically over the sheath 12 and thus also over the inner catheter 14. The collet clamp 64 has, in conventional manner, a plurality of proximal extending arms, coupled to one another at their distal ends, the arms including radially outwardly extending shoulders having bevelled surfaces, as shown in the FIGURE. The arms of the collet clamp 64 are able to be biased towards one another so as to be squeezed radially inwardly, thereby to squeeze radially inwardly any element held thereby, in this case the sheath 12.

It will be apparent from the FIGURE that when the locking cap 50 is rotated towards the locking condition, that is screwed towards the unit 42, the inner surface 66 of the locking cap 50 will press the collet clamp 64 towards the end 56 of the unit 42 and thereby cause the arms of the collet clamp 64 to be biased to their compressed and closing configuration. On the other hand unscrewing of the locking cap 50 will move the inner wall 66 of the locking cap 50 away from the end 56 of the unit 42 thereby allowing the arms of the collet clamp 64 to spring outwardly as a result of the natural resilience of the collet clamp 64, thereby towards a releasing condition.

The configuration of the handle assembly 10 shown in the FIGURE is that adopted for transportation and prior to use of the introducer assembly. Specifically, in such a configuration, the locking cap 50 is in a locking condition, thus in which it biases the collet clamp 64 into a clamping configuration and in which the flushing shield 60 overlies the luer fitting 46.

The clamping action of the collet clamp 64 presses the sheath 12 at this location against the inner element 14 (the latter having a compressive strength greater than the compressive strength of the collet clamp 64), thereby to clamp the sheath 12 to the carrier element 14. This has the effect of closing or substantially closing any space between the sheath 12 and the inner element 14, in a fluid tight or substantially fluid tight manner In addition, such clamping action prevents any movement of the sheath 12 relative to the carrier element 14. In such a configuration, depression of the trigger 26, even though this would release the drum 22 for rotation by the spring 24, will have no action as a result of the clamping of the sheath 12. In some embodiments there may be provided additional safety catches to prevent operation of the trigger during transportation although this is not necessary in the preferred embodiment.

In the locking configuration also, therefore, the flushing apertures 48 in the sheath 12 provide a passage only to the space distal of the clamping of the collet clamp 64, given that the clamp 64 provides effectively a seal at its location which prevents flow of flushing fluid in a proximal direction into the casing 20.

In this embodiment, the locking cap 50 provides two unlocking conditions. In the first, the flushing shield 60 is moved away from the luer fitting 46 to enable a syringe or other source of flushing fluid to be coupled to the fitting 46. In this configuration, the collet clamp 64 remains in a clamping condition. When the luer fitting 46 is thus released, flushing fluid can be fed through the conduit 44 into the chamber 42 and thereby through the flushing apertures 48 into the space between the sheath 12 and inner catheter 14. The seals 38, 40 prevent the flushing fluid from escaping from within the chamber 42, while the collet clamp 64 prevents flushing fluid passing proximally through the sheath 12. Thus, flushing fluid fed into the chamber 42 can flush the entirety of the space between the sheath 12 and the carrier element 14, all the way to the distal end of the introducer assembly.

The introducer assembly is then inserted into the patient until its distal end, which carries the implantable medical device or medical treatment tool, is positioned at the treatment site. The handle assembly 10 is then reconfigured to allow for deployment of the medical device. Specifically, the locking cap 50 is rotated further in an opening direction so as to release the closing pressure on the collet clamp 64. This action allows the arms of the collet clamp 64 to spring to their outward, rest, position and thereby to releases their grip on the sheath 12. Once so released, actuation of the trigger 26 will disengage the drum 22 so as to allow the latter to rotate under the force of the spring 24. Rotation of the drum 22 will cause the proximal end 28 of the sheath 12 to wind onto the drum. This winding in turn causes the sheath 12 to be pulled backwards, in a proximal direction, and across the cutting blade 30. As it passes the cutting blade 30, the sheath is split and can thus be drawn away from the inner element 14 towards the drum 22. Backward movement of the sheath 12 causes it to expose the medical device (or treatment tool) at the distal end of the introducer assembly, thereby to allow the latter to be deployed.

The trigger 26 is preferably of a type which, when released, can again stop rotation of the drum 22, thereby providing for controlled withdrawal of the sheath 12. Typically, this may be by reengagement of the teeth of these components. For this purpose, the trigger 26 is preferably provided with a return spring or like element which biases it towards the locking position.

The handle assembly and introducer described above and shown in the FIGURE provide an effective automatic mechanism for retracting the sheath and in particular for allowing an extensive length of sheath to be retracted within a compact handle assembly, avoiding the need to pull great distances beyond the proximal end of the introducer assembly. The assembly does so by a split-sheath arrangement and has a structure and form in which the sheath can be effectively and conveniently flushed prior to operation of the introducer assembly. The handle assembly also provides convenient mechanism for locking the sheath in position until the introducer assembly is ready to be deployed.

It is to be appreciated that various modifications may be made to the described embodiments. Examples include the design of the cutting blade, the locking cap, as well as of the flushing shield 60. For instance, the cutting blade could be a fixed blade as shown in the drawing or could be a movable blade which is only placed in a cutting position once it is desired to operate the assembly. Similarly, the flushing shield 60 could be an annular or cylindrical element disposed around the luer fitting 46, with one or more apertures therein which by rotation can be suitably aligned with the luer fitting to give/prevent access to thereto at the appropriate stages of locking of the cap 50. Similarly, the shield 60 could allow access to the luer fitting 46 at all configurations in which the locking cap 50 is in a locking condition. The shield 60 need not be rotatable with the locking cap 50, it could for instance be pivotably movable on a support arm or movable in any other suitable way.

The handle assembly 10 is useful for the deployment of a wide variety of implantable medical devices, including stents, stent grafts, vena cava filters, occlusion devices and so on, and can also be used with medical treatment implements.

It is to be understood that although the dependent claims are set out in single dependent form, the features of the dependent claims can be combined with one another as if they were in multiply dependent form.

What is claimed is:

1. An introducer assembly for the deployment of an implantable medical device, the assembly including:
   a proximal end and a distal end;
   a sheath;
   a carrier element for carrying a medical device at the distal end of the assembly, the carrier element being locatable in the sheath;
   a flushing unit located over the sheath at the proximal end of the assembly, the flushing unit including a flushing fluid chamber provided with first and second seals on either end thereof, the seals sealing over the sheath, the sheath being provided with at least one hole therein located in the flushing fluid chamber, and a sealing element located proximally of the flushing chamber for sealing the proximal end of the sheath and preventing movement of the sheath relative to the carrier;
   wherein fluid can be flushed from the flushing fluid chamber to between the sheath and the carrier element.

2. An assembly according to claim 1, wherein the sheath is a splittable sheath.

3. An assembly according to claim 2, including a manipulation unit at the proximal end of the assembly, wherein the flushing unit forms part of the manipulation unit, the manipulation unit including a splitting element operable to split of the sheath, said splitting element being located proximal of the flushing unit.

4. An assembly according to claim 3, wherein the splitting element includes a blade arranged to cut the sheath in a longitudinal direction.

5. An assembly according to claim 3, including a reel onto which split sheath material can be wound.

6. An assembly according to claim 5, wherein the reel is sprung to rotate.

7. An assembly according to claim 6, including a control actuator for controlling the rotation of the reel.

8. An assembly according to claim 7, wherein the control actuator includes a trigger element.

9. An assembly according to claim 1, wherein the sealing element includes a compression element arranged to compress the sheath onto the carrier element, thereby to close the space between the sheath and the carrier element at the location of the compression element.

10. An assembly according to claim 9, wherein the compression element includes a collet clamp.

11. An assembly according to claim 10, wherein the collet clamp is sprung, providing a biasing force towards an open configuration.

12. An assembly according to claim 11, further comprising a driving element for driving the collet clamp towards a closed configuration.

13. An assembly according to claim 12, wherein the driving element is threaded, which thread provides movement of the driving element.

14. An assembly according to claim 12, wherein the flushing unit includes a port for coupling to a source of flushing fluid, the driving element including a barrier element which overlies the port when the driving unit is in a configuration other than that which closes the compression element.

15. An assembly according to claim 14, wherein the barrier element includes a shield for covering the port.

16. An assembly according to claim 9, wherein the compression element, when engaged, prevents movement of the sheath in the assembly.

17. An assembly according to claim 1, wherein the seals are annular elastomeric seals disposed around the sheath.

18. An introducer assembly for the deployment of an implantable medical device, the assembly including:
    a proximal end and a distal end;
    a splittable sheath;
    a carrier element for carrying a medical device at the distal end of the assembly, the carrier element being locatable in the sheath with a space therebetween;
    a flushing unit located over the sheath at the proximal end of the assembly, the flushing unit including a flushing fluid chamber provided with first and second seals on either end thereof, the seals sealing over the splittable sheath, the splittable sheath being provided with at least one hole therein located in the flushing fluid chamber, and a sealing element located proximally of the flushing chamber for sealing the proximal end of the sheath, the sealing element including a collet clamp arranged to compress the sheath onto the carrier element, thereby to close the space between the sheath and the carrier element at the location of the collet clamp and to prevent movement of the sheath relative to the carrier;
    a manipulation unit at the proximal end of the assembly, wherein the flushing unit forms part of the manipulation unit, the manipulation unit including means to cause splitting of the sheath, said splitting means being located proximal of the flushing unit;
    the manipulation unit including a drum onto which split sheath material can be wound;
    wherein fluid can be flushed from the flushing fluid chamber into the space between the sheath and the carrier element.

* * * * *